(12) United States Patent
Burton et al.

(10) Patent No.: US 9,255,071 B2
(45) Date of Patent: Feb. 9, 2016

(54) COMPOUNDS HAVING ANTIBACTERIAL ACTIVITY, PROCESS FOR THEIR PREPARATION AND PHARMACEUTICAL COMPOSITIONS COMPRISING THEM

(71) Applicants: Consejo Nacional de Investigaciones Cientificas y Técnicas (CONICET), Buenos Aires (AR); Laboratorios Richmond Sociedad Anónima Comercial Industrial y Financiera, Buenos Aires (AR)

(72) Inventors: Gerardo Burton, Olivos (AR); Fernando Javier Duran, Buenos Aires (AR); Mario David Martinez, Merlo (AR); Elvira Zini, Buenos Aires (AR); Veronica Mora Munoz, Buenos Aires (AR); Lucila Bertoncello, Buenos Aires (AR)

(73) Assignees: Consejo Nacional de Investigaciones Cientificas y Técnicas (CONICET), Buenos Aires (AR); Laboratorios Richmond Sociedad Anónima Comercial Industrial y Financiera, Buenos Aires (AR)

( * ) Notice: Subject to any disclaimer, the term of this patent is extended or adjusted under 35 U.S.C. 154(b) by 0 days.

(21) Appl. No.: 14/371,820

(22) PCT Filed: Jan. 10, 2013

(86) PCT No.: PCT/IB2013/050235
§ 371 (c)(1),
(2) Date: Jul. 11, 2014

(87) PCT Pub. No.: WO2013/105053
PCT Pub. Date: Jul. 18, 2013

(65) Prior Publication Data
US 2014/0357678 A1    Dec. 4, 2014

(30) Foreign Application Priority Data

Jan. 11, 2012    (AR) ............... 20120100090

(51) Int. Cl.
| | |
|---|---|
| *C07D 213/86* | (2006.01) |
| *C07C 235/34* | (2006.01) |
| *C07C 51/60* | (2006.01) |
| *C07C 231/02* | (2006.01) |
| *C07C 235/38* | (2006.01) |
| *C07C 51/347* | (2006.01) |
| *C07C 259/08* | (2006.01) |
| *C07D 213/81* | (2006.01) |
| *C07D 295/185* | (2006.01) |

(52) U.S. Cl.
CPC ........... *C07D 213/86* (2013.01); *C07C 51/347* (2013.01); *C07C 51/60* (2013.01); *C07C 231/02* (2013.01); *C07C 235/34* (2013.01); *C07C 235/38* (2013.01); *C07C 259/08* (2013.01); *C07D 213/81* (2013.01); *C07D 295/185* (2013.01); *C07C 2101/14* (2013.01)

(58) Field of Classification Search
CPC  C07C 2101/14; C07C 231/02; C07C 235/34; C07C 235/38; C07C 259/08; C07C 51/347; C07C 51/60; C07D 213/81; C07D 213/86; C07D 295/185

See application file for complete search history.

(56) References Cited

U.S. PATENT DOCUMENTS

| | | | | |
|---|---|---|---|---|
| 5,707,997 | A * | 1/1998 | Shoji ............... | C07D 487/04 514/259.3 |
| 5,859,025 | A * | 1/1999 | Wagner ............ | C07D 215/26 514/311 |
| 6,025,349 | A * | 2/2000 | Schwark ........... | C07C 279/22 514/182 |
| 6,046,239 | A * | 4/2000 | Lennox ............ | A61K 31/192 514/349 |
| 6,239,077 | B1 * | 5/2001 | Andoh ............. | A01N 37/26 504/312 |
| 2006/0111357 | A1 * | 5/2006 | Frimurer ........... | A61K 31/435 514/249 |

FOREIGN PATENT DOCUMENTS

| | | | | |
|---|---|---|---|---|
| GB | EP 0194764 | A1 * | 9/1986 | ............ A01N 37/18 |
| IT | EP 0581165 | A2 * | 2/1994 | ............ C07D 451/04 |

\* cited by examiner

*Primary Examiner* — Joseph Kosack
*Assistant Examiner* — Amanda L Aguirre
(74) *Attorney, Agent, or Firm* — Greer, Burns & Crain, Ltd.

(57) ABSTRACT

A pharmaceutically acceptable salt, prodrug or derivative compound of the formula I, wherein $R_1$ is selected from H, a (C1-C5) alkyl group and a $COR_4$ group; $R_2$ is selected from H, a (C1-C5) alkyl group and a $COR_5$ group; $R_3$ is selected from H, a (C1-C5) alkyl group, a (C1-C5)-O-alkyl group, a cycloalkyl of (C5-C6) carbon atoms, an aryl group, and an aryl (C1-C5) alkyl group wherein the aryl group can be an unsubstituted aryl or substituted with one or more $R_6$ groups and an $NHCOR_5$ group, or the $R_2$ and $R_3$ groups together with N may form a piperidine, morpholine or piperazine group; $R_4$ is selected from H and a (C1-C5)alkyl group; $R_5$ is selected from an aryl group unsubstituted or substituted with one or more $R_6$, linear or branched(C1-C5) alkyl or pyridyne groups and a pyridine group; $R_6$ is selected from (C1-C5)alkyl groups, halogen and nitro.

14 Claims, 2 Drawing Sheets

COMPOUNDS HAVING ANTIBACTERIAL ACTIVITY, PROCESS FOR THEIR PREPARATION AND PHARMACEUTICAL COMPOSITIONS COMPRISING THEM

The present invention relates to novel compounds having antimicrobial activity, the processes for their preparation and the pharmaceutical compositions comprising them.

BACKGROUND

Antimicrobial resistance, which entails the microorganisms ability to find ways aimed at circumventing the actions of the drugs used to cure the infections caused by such microorganisms, is held as a current public health issue not only because of the growing trend of resistant bacteria, but also due to the lack of new antibiotics [ECDC/EMEA Joint Technical Report; The bacterial challenge: time to react. *A call to narrow the gap between multidrug-resistant bacteria in the EU and the development of new antibacterial agents*; September 2009].

Back in 2004, the World Health Organization (WHO) initially envisaged a future lacking effective antibiotics and asserted that resistance to antibiotics is one of three most serious threats to all mankind. [W. Kaplan, R. Laing, Priority Medicines for Europe and the World; World Health Organization; Department of Essential Drugs and Medicines Policy, November 2004]. In turn, there is a growing demand of antibiotics not only due to the resistance issue, but also to the extended life expectancy of the population, a higher infection rate and an increasing number of immunocompromised patients.

According to the WHO, deaths caused by acute respiratory infections, diarrheas, measles, HIV, malaria and tuberculosis account for 85% of mortality due to infections. Resistance against first-line treatment drugs for the majority of these pathogens giving rise to the above mentioned diseases ranges from 0 to 100%. Additionally, resistance has been found to occur with second or third-line treatment drugs, which therefore exerts an impact on these diseases therapy. Furthermore, importance is to be attached to resistance emerging from intrahospital infections strains. People's growing inter-country mobility rate not only has increased the spread of infectious diseases but also the risk of resistance. Not only does resistance affect people's quality of life, but it also claims their lives, entails Public Health Institutions monetary investments in various countries, and results in healthcare plans proving inefficient and uncertain.

Multi-drug resistant Gram-positive bacteria (MDRGP) still continue to pose challenges to the scientific community, which involve both *Staphylococcus aureus*, whose first penicillin-resistant strains emerged in the 50's and recent cases such as penicillin-resistant *Streptococcus pneumoniae* and *Mycobacterium tuberculosis*-resistant strains (specifically involving acid-resistant Gram-positive bacteria). It is worth highlighting that roughly 500,000 patients are yearly diagnosed with multiple-drug resistant tuberculosis and 110,000 of them encounter death. The multiple-drug resistant Gram-negative bacteria (MDRGN) have turned into an issue of concern over the last years, particularly, the *E. coli*-resistant strains.

Antimicrobial resistance also poses a threat to further healthcare breakthroughs over the last years. Thus, co-infections with HIV and resistant pathogens, tuberculosis, salmonellosis and other sexually transmitted diseases may feature a rapidly-advancing spread and progression and a potential multiplier effect on resistance transmission. A disease like tuberculosis, which had become completely treatable and controllable, has turned into a menace over again. 3.6% of the worldwide occurring tuberculosis cases have proved resistant to the regularly administered antibiotics.

Therefore, the search for new chemical entities with antimicrobial properties and structures differing from those found in conventional antibiotics is viewed as a pressing need to develop new ways to curb these resistant infections. The caffeic acid (3,4-dihydroxycinnamic acid) and its esters, are phenolic compounds widely distributed in the plant kingdom. The majority of these compounds feature antibacterial, antiviral, anti-sclerotic, anti-HIV and anti-tumor activities, among others. The caffeic acid structure also makes up the central core of hygromycin A, a broad-spectrum antibiotic obtained from *Streptomyces hygroscopicus* [R. C. Pittenger, R. N. Wolfe, P. N. Hoehn, W. A. Daily, J. M. McGuire, *Antibiot. Chemother.*, 3 (1953) 1268-1278]. Results from various recently developed investigations involving the testing of simple caffeic amides and related compounds with significant antibacterial activity against *Mycobacterium tuberculosis* resistant strains [G. K. Yoya, F. Bedos-Belval, P. Coonstant, H. Durán, M. Daffé, M. Baltas, *Bioorg. Med. Chem. Lett.*, 18 (2008) 538-541; J. Fu, K. Cheng, Z-M. Zhang, R-Q. Fang, H-L. Zhu, *Eur. J. Med. Chem.*, 45 (2010) 2638-2643] and *Staphilococcus aureus* [R. J. Herr, *Bioorg. Med. Chem.*, 10 (2002) 3379-3393; B.-e. Yingyongn-arongkul, N. Apiratikul, N. Aroonrerk, A. Suksamram, *Bioorg. Med. Chem. Lett.*, 16 (2006) 5870-5873], are currently available. Some of the Its simple structure and the ease with which functional and structural changes may be carried out, make caffeic acid an ideal scaffold to develop new families of compounds.

Biological activity studies have shown certain structural characteristics that are to be found in the caffeic acid active derivatives; particularly, the unprotected phenolic hydroxyls at positions 3 and 4 of the aromatic ring that provide the redox couple responsible for their antioxidant activity, and the carboxyl group forming amides with aliphatic or aromatic amines in the specific case of antibacterial activity.

SUMMARY

A compound having the following structural formula I:

Formula I a pharmaceutically acceptable salt, prodrug or derivative thereof, wherein $R_1$, $R_2$ and $R_3$ have the meanings indicated below. The compounds of the invention have antibacterial activity.

The invention also refers to the pharmaceutical compositions comprising such compounds, the processes for their obtention and the methods of treatment that comprise administering them.

BRIEF DESCRIPTION OF THE FIGURES

The FIG. 1 shows the 3-difluoromethyl-4-methoxy cinnamyl fluoride (VII) $^1$H (FIG. 1A) and $^{13}$C (FIG. 1B) NMR spectra, intermediate isolated from the solution after silica gel percolation, which is useful to obtain the compounds of the invention.

DETAILED DESCRIPTION

The inventors of the present invention have found that the combination of a protected hydroxyl at C-4 position with a difluoromethyl group at C-3 leads to the obtention of more active caffeic acid analogs, several of which show high antibacterial selectivity against *Mycobacterium*.

It is an object of the present invention, a compound having the following structural formula I:

Formula I a pharmaceutically acceptable salt, prodrug or derivative thereof, characterized in that $R_1$ is selected from H, a linear or branched (C1-C5) alkyl group and a $COR_4$ group; $R_2$ is selected from H, a linear or branched (C1-C5) alkyl group and a $COR_5$ group; $R_3$ is selected from H, a linear or branched (C1-C5)alkyl group, a linear or branched (C1-C5)-O-alkyl group, a cycloalkyl of (C5-C6) carbon atoms, an aryl group, and an aryl (C1-C5) alkyl group wherein the aryl group can be an unsubstituted aryl or an aryl substituted with one or more $R_6$ groups and an $NHCOR_5$ group, or the $R_2$ and $R_3$ groups together with the N may form a substituted or unsubstituted piperidine, morpholine or piperazine group; $R_4$ is selected from H and a (C1-C5) alkyl group; $R_5$ is selected from an unsubstituted aryl group or an aryl group substituted with one or more $R_6$ groups, linear or branched(C1-C5) alkyl or pyridyl groups and a pyridyl group; $R_6$ is selected from (C1-C5)alkyl groups, halogen and nitro, provided that $R_1$, $R_2$ and $R_3$ are not H atoms at the same time.

Additionally, it is another object of the invention a pharmaceutical composition comprising at least one compound of formula I and pharmaceutically acceptable excipients.

Furthermore, it is another object of the invention a process usable to obtain the compounds of formula I.

Moreover, the present invention discloses methods for the treatment of infections in patients in needs thereof, which comprises the administration of a therapeutically effective amount of at least one compound of formula I. The invention further comprises the administration of a compound of formula I, with other therapeutically active compounds, and, particularly, with other antibiotic or antibacterial compounds. According to another embodiment of the invention, the administration of a compound of formula I in animals shall apply. In other words, the invention compounds may be administered both in human beings and in animals of various species. Therefore, the invention encompasses the use of the compounds for human therapy and in veterinary applications.

According to the present invention, the term "administer" as well as the variants thereof (for instance, the "administration" of a compound) regarding an invention compound, means the introduction of a compound, prodrug, salt or pharmaceutically acceptable derivative of such invention compound into the system of the animal or human being in need of such treatment. When the invention compound, salt or pharmaceutically acceptable derivative of such compound is used in combination with one or more active agents (like another antibiotic), the terms "administration" and the variants thereof shall each be construed as involving the sequential and concurrent introduction of the compound, salt, derivative or prodrug thereof, and of other agents.

For the purposes of the present invention, the term "Patient" shall apply to humans. Nevertheless, it should be noted that compounds may also be administered in other animals, particularly, mammals and other organisms. Therefore, the above mentioned methods shall be employed both for human therapy and veterinary applications.

As a result, in some particular realizations, compounds are to be administered in mammals, whereas in some others they shall be used in humans.

The technical expert shall be able to understand that the invention compounds, due to their antibacterial activity, may be used other than for pharmaceutical purposes such as in nourishing, cleaning and cosmetic formulations, etc.

Given the chemical structure of the invention compounds, and their log P standing close to 3, they may be employed in pharmaceutical formulations like tablets and suspensions. Furthermore, the groups with basic nitrogens in the substituents are subject to undergo salification in order to obtain water-soluble derivatives that may be used in other pharmaceutical formulations.

According to the present invention, a "pharmaceutically acceptable salt" of a given compound refers to a salt that is pharmaceutically acceptable and has the desired pharmacological activity of the starting compound. Pharmaceutically acceptable salts shall be held to be non-toxic. Additional information concerning suitable pharmaceutically acceptable salts may be found in *Remington's Pharmaceutical Sciences*, $17^{th}$ ed., Mack Publishing Company, Easton, Pa., 1985, which is enclosed herein as reference literature. The invention compounds shall be understood to have one or more pharmaceutically acceptable salts associated with them.

The term "prodrug" makes reference to such compounds that are transformed in vivo (generally rapidly) in order that starting compound of the above mentioned formula may be obtained, for instance by means of blood hydrolysis. The expert in the technique shall have adequate knowledge to prepare prodrugs of the invention compounds following the procedures suitable to that effect.

"A therapeutically effective quantity of" involves a given amount of the invention compound providing effective disease treatment upon being administered to patients. The amount of the invention compound making up a "therapeutically effective quantity of" shall vary depending on a set of variables like the compound activity, the metabolic stability, the excretion rate, the compound action duration, as well as the patients' age, weight, general health condition, sex, diet, type of patients involved, the method and length of compound administration, the concurrent administration of adjuvants or additional therapies and the severity of the disease for which a therapeutic effect is sought.

The therapeutically effective amount for a specific case may be determined with no further experiments proving applicable. In preferred realizations, the acceptable dosage range stands between 100 mg and 200 mg administered every 24 hours on an oral, intramuscular o intravenous basis. As well-known in the art, it may prove applicable to make adjustments to the local vs systemic release, the patients' age, weight, general health condition, sex, diet, type of patients involved, the method and length of compound administration, the concurrent administration of adjuvants or other therapeutically active ingredients and the severity of the disease for which a therapeutic effect is sought. Such parameters shall be ascertained by conducting the usual routine tests.

A patient may be administered the invention compounds by means of any acceptable route of administration. Acceptable routes of administration include, but are not limited to oral, parenteral, transdermal, endocervical, endosinusal, enteral, intra-abdominal, intraarterial, intrabronchial, intracerebral, intracoronary, intradermal, intraductal, intraduodenal, intradural, intraepidermal, intraesophagic, intragastric, intragingival, intraileal, intralymphatic, intrameningeal, intramuscular, intraovarian, intraperitoneal, intraprostatic, intrapulmonary, intrasinal, intraspinal, intrasinovial, intratesticular, intrathecal, intratubular, intratumoral, intrauterine, intravascular, intravenous, nasal, nasogastric, buccal, percutaneal, peridural, rectal, respiratory (inhalation), subcutaneous, sublingual, submucosal, topical, transmucosal, transtracheal, ureteral, urethral and vaginal routes.

The invention compounds may be administered at any acceptable solid, half-solid, liquid or gas dosage form. Acceptable dosage forms include but are not limited to tablets, capsules, solutions, sprays, creams, emulsions, gases, gels, grains, liniments, lotions, suppositories, ointments, pastes, powders, suspensions, syrups and pills.

A dosage form of the invention may comprise either solely the invention compound, or such compound may be formulated with conventional excipients, pharmaceutical supports, adjuvants and/or other medicinal or pharmaceutical agents. Acceptable excipients involve but are not limited by (a) anti-adherents like sodium croscarmellose, crospovidone, sodium starch glycolate, microcrystalline cellulose, starch and talc; (b) binding agents like cellulose, gelatine, hydroxypropyl cellulose, lactose, polyethyleneglycol, polyvinylpyrrolidone, sorbitol, starch and xylitol; (c) coating agents such as cellulose and shellac; (d) desintegrating agents like cellulose, polyvinylpyrrolidone, sodium carboxymethyl cellulose, methyl cellulose, microcrystalline cellulose, sodium starch glycolate and starch; (e) filling agents such as calcium carbonate, cellulose, dibasic calcium phosphate and mannitol; (f) flavoring agents; (g) coloring agents; (h) glidants like calcium stearate and colloidal silicon dioxide; (i) lubricants such as calcium stearate, magnesium stearate, polyethyleneglycol, and talc; and (j) preservation agents like citric acid, vitamin C and vitamin E. The pharmaceutical supports include soluble polymers, insoluble or biodegradable natural or synthetic polymer microparticles, microcapsules, lipoproteins, liposomes and micelles.

The invention pharmaceutical composition shall include a therapeutically effective amount of the invention compound, a prodrug, a derivative or a pharmaceutically acceptable salt of such derivative; the remainder of the pharmaceutical composition containing one or more pharmaceutically acceptable excipients. An invention compound, a prodrug, a derivative or a pharmaceutically acceptable salt of such derivative shall generally fall within a 1%-99% ratio of the pharmaceutically acceptable composition weight; the remainder of the pharmaceutically acceptable composition containing one or further pharmaceutically acceptable excipients.

An invention compound, an individual stereoisomer of such compound or the mixture of the compound stereoisomers, a prodrug, a derivative or a pharmaceutically acceptable salt of such derivative shall generally fall within a 5%-75% ratio of the pharmaceutically acceptable composition weight; the remainder of the pharmaceutical composition containing one or more pharmaceutically acceptable excipients. The methods to prepare the invention dosage forms are well-known, or shall be ostensible to technical experts; for instance, see *Remington's Pharmaceutical Sciences,* 18th Ed., (Mack Publishing Company, Easton, Pa., 1990).

A "therapeutically effective quantity of" an invention compound shall vary depending on a set of variables like the compound activity, the metabolic stability, the excretion rate and the compound action duration, the patients' age, weight, general health condition, sex, diet, and type of patients involved, the method and length of compound administration, the presence of adjuvants and of additional therapeutically active ingredients in the composition, and the severity of the disease for which a therapeutic effect is sought.

Many compounds have been synthesized and their antibacterial activity has been assessed by one or more of the assays outlined in the strains panel in Table 3 shown below. The description of the most representative compounds and the activity observed is shown in Table 1 (entries 1-14). The comparison of entries 15-17 in Table 1 with entry 3, show an enhanced activity and selectivity due to the difluoromethyl substituent.

TABLE 1

Antibacterial activity of amides of 3-difluoromethyl-4-methoxycinnamic acid and related compounds.

| | Compound | Microorganism | MIC (µg/ml) |
|---|---|---|---|
| 1 | | *M. smegmatis* | 64 |

TABLE 1-continued

Antibacterial activity of amides of 3-difluoromethyl-4-methoxycinnamic acid and related compounds.

| | Compound | Microorganism | MIC (µg/ml) |
|---|---|---|---|
| 2 | (structure) | *M. smegmatis* | 8 |
| 3 | (structure) | *M. smegmatis* | 64 |
| 4 | (structure) | *M. smegmatis* <br> *C. sporogenes* | 64 <br> 64 |
| 5 | (structure) | *M. smegmatis* | 32 |
| 6 | (structure) | *M. smegmatis* <br> *S. pneumoniae* | 8 <br> 64 |
| 7 | (structure) | *S. pneumoniae* | 64 |
| 8 | (structure) | *M. smegmatis* | 32 |

TABLE 1-continued

Antibacterial activity of amides of 3-difluoromethyl-4-methoxycinnamic acid and related compounds.

| | Compound | Microorganism | MIC (µg/ml) |
|---|---|---|---|
| 9 | | M. smegmatis | 32 |
| 10 | | S. flexneri | 32 |
| | | S. boydii | 32 |

In the specific object of the invention, such invention is related to a procedure intended to prepare the amides of 3-difluoromethyl-4-methoxycinnamic acid of general formula II, wherein $R_1$ may either be alkyl, cycloalkyl, aryl, alcoxyl or aroylamine and $R_2$ may be hydrogen or methyl, or $R_1$ and $R_2$ may be part of a ring. An identical procedure shall apply in order to obtain dimers of type III or IV.

M. White, A. R. Tunoori, B. J. Turunen, G. I. Georg, J. Org. Chem., 69, 2573-2576 (2004)]. This limitation is particularly relevant in the case of unreactive amines or if an excess of Deoxo-Fluor® is used, and such limitation in the case described here gives rise to N,N-bis(2-methoxymethyl)-3-(difluoromethyl)-4-methoxycinnamyl amide (II with $R_1=R_2=CH_2CH_2OCH_3$).

(n = 0 a 5)

As described in Table 1, various amides of 3-difluoromethyl-4-methoxycinnamic acid show significant selective antimicrobial activity against *Mycobacterium*. The preparation of such compounds, on the one hand, requires the introduction of the difluoromethyl group into the 4-methoxycinnamic acid molecule and, on the other, the formation of the corresponding amide. It is known that the difluoromethyl group may be obtained by the reaction of an aldehyde group with a fluorinating reagent like bis[(2-methoxyethyl)amino] sulfur trifluoride (Deoxo-Fluor®) or bis(ethylamino)sulfur trifluoride (DAST). Also, the preparation of acyl fluorides from carboxylic acids and Deoxo-Fluor® and their subsequent transformation into amides by reaction with amines has been described. A limitation of the latter preparation is the competitive reaction of the acyl fluoride with bis(2-methoxyethyl)amine, a byproduct of Deoxo-Fluor® fluorination. [J.

According to special realizations of the present invention, the foregoing limitation may be eliminated by percolating the mixture from the fluorination reaction through a silica gel bed which produces an acyl fluoride solution free from contaminating by-products and enables the subsequent reaction with various free and salified amines, even when an excess of the fluorinating agent is used, or a prolonged reaction time or higher temperature is required due to the amine low reactivity. An additional advantage of this procedure lies in the fact that it achieves two simultaneous fluorination reactions on the same molecule in a single step, as are the transformations of an aldehyde group into a difluoromethyl group and concurrently that of the carboxyl group into an acyl fluoride, as well as the subsequent transformation of such fluoride into an amide with no interference from the by-products resulting from carrying out both reactions.

In order to implement this procedure, 2-methoxy-5-iodobenzaldehyde (V) was used as starting material, which, through a Heck-type reaction with methyl acrylate followed by in situ hydrolysis of the ester gave 3-formyl-4-methoxycinnamic acid (VI). Alternatively, the coupling reaction may be carried out with acrylic acid, therefore avoiding the hydrolysis step. The 3-formyl-4-methoxycinnamic acid (VI) was reacted with 3 equivalents of Deoxo-Fluor® solution in toluene or tetrahydrofuran, preferably Deoxo-Fluor® 50% in toluene. Dichloromethane the is the preferred reaction solvent between 0° and a reflux temperature, preferably 25Ω. Upon completion of the reaction (determined by thin-layer chromatography) the mixture is diluted with dichloromethane and percolated through a silica gel bed under an inert atmosphere to remove the by-products from the fluorination reaction, giving a solution of 3-difluoromethyl-4-methoxy cinnamyl fluoride (VII).

Figure 1:
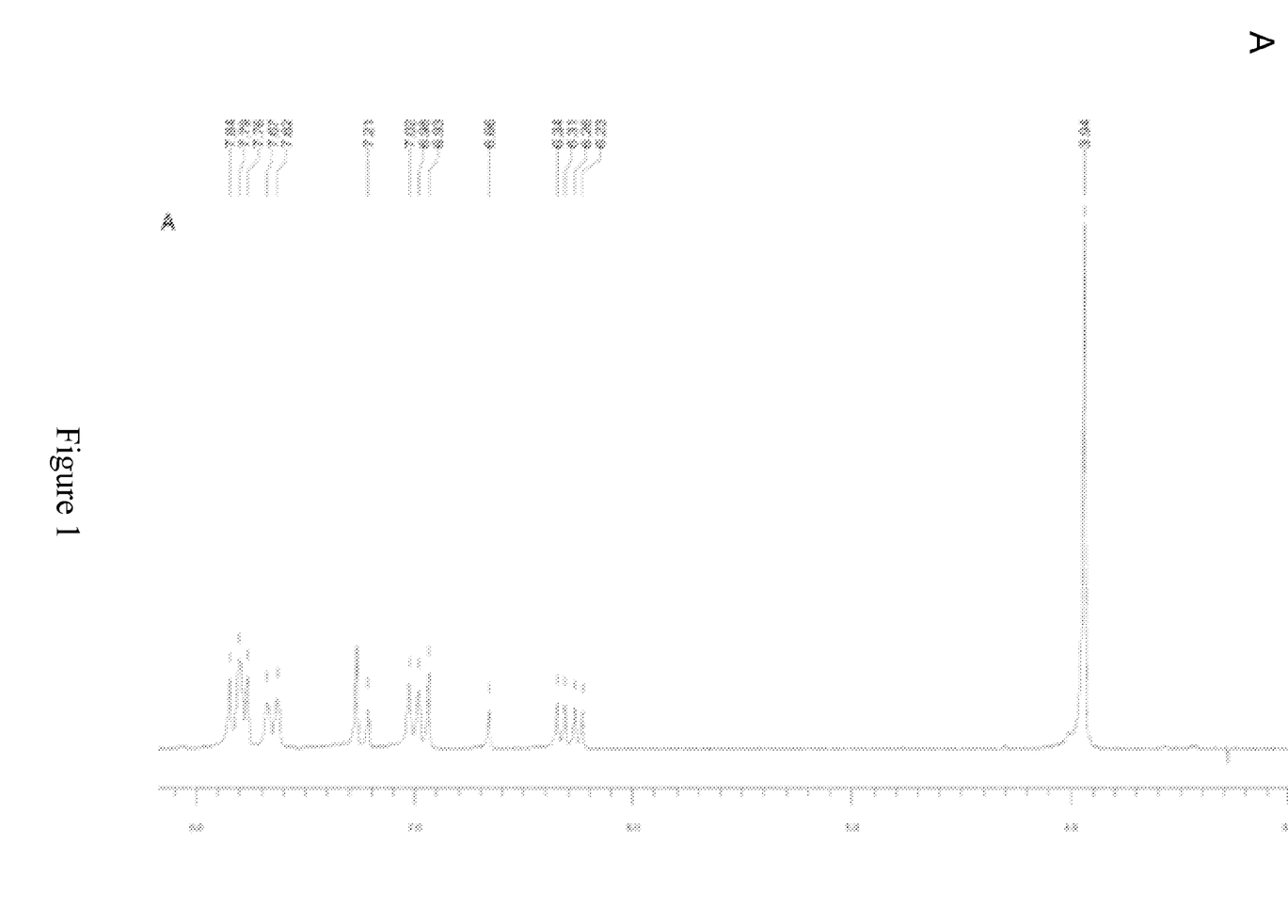

This intermediate was identified by its $^1$H and $^{13}$C NMR spectra (FIG. 1 and Table 2) even though its isolation is not required.

TABLE 2

Assignment of NMR signals of 3-difluoromethyl-4-methoxycinnamyl fluoride (VII).

| | $^{13}$C NMR | $^1$H NMR |
|---|---|---|
| 1 | 125.9 | — |
| 2 | 126.7 (t, $J_{CF}$ 6.0 Hz) | 7.79 (1H, s) |
| 3 | 123.7 (t, $J_{CF}$ 22 Hz) | — |
| 4 | 159.9 (t, $J_{CF}$ 6.0 Hz) | — |
| 5 | 111.5 | 7.00 (1H, d, J 8.6 Hz) |
| 6 | 133.0 | 7.65 (1H, d, J 8.6 Hz) |
| 1' | 157.2 (d, $J_{CF}$ 338 Hz) | — |
| 2' | 110.7 (d, $J_{CF}$ 68 Hz) | 6.29 (1H, dd J 7.1, 15.7 Hz) |
| 3' | 150.1 (d, $J_{CF}$ 6.3 Hz) | 7.80 (1H, d, J 16.0 Hz) |
| CF$_2$ | 110.8 (t, $J_{CF}$ 236 Hz) | 6.93 (1H, t, J 55 Hz) |
| OCH$_3$ | 56.0 | 3.94 (3H, s) |

Amides are prepared directly from the 3-difluoromethyl-4-methoxycinnamyl fluoride (VII) solution by adding the primary or secondary amine and a tertiary amine, such as triethylamine or equivalent as an acid acceptor.

A full description of the entire procedure is provided on scheme 1. The method proves versatile enough to allow the alternative use of a salt of the primary or secondary amine such as a hydrochloride or acetate, provided that a sufficient quantity of acid acceptor is added. In the event of using diamines, such as piperazine or 1,3-propanediamine in an adequate stoichiometric ratio, dimers III and IV (n=3) respectively are obtained. When using 2-acetyloxy-5-iodobenzaldehyde as starting material, analogs of II acetylated at position 4 are obtained.

Scheme 1. Synthesis of 3-(difluoromethyl)-4-methoxycinnamic acid amides

Following is a list of specific amides, which serves as a thorough overview of the versatility achieved by this invention:
N-methyl-3-(difluoromethyl)-4-methoxycinnamyl amide
N-isopropyl-3-(difluoromethyl)-4-methoxycinnamyl amide
N-methoxy-N-methyl-3-(difluoromethyl)-4-methoxycinnamyl amide
N-isobutyl-3-(difluoromethyl)-4-methoxycinnamyl amide
N-isopentyl-3-(difluoromethyl)-4-methoxycinnamyl amide
N-(2-phenylethyl)-3-(difluoromethyl)-4-methoxycinnamyl amide
N-phenyl-3-(difluoromethyl)-4-methoxycinnamyl amide
N-ciclohexyl-3-(difluoromethyl)-4-methoxycinnamyl amide
N-[3-(difluoromethyl)-4-methoxycinnamoyl]-N'-(isonicotinoyl)hydrazine
N-[3-(difluoromethyl)-4-methoxycinnamoyl]morpholine
N,N'-bis[3-(difluoromethyl)-4-methoxycinnamoyl]piperazine
N,N'-bis[3-(difluoromethyl)-4-methoxycinnamoyl]-1,3-propanamine
N-isopropyl-3-(difluoromethyl)-4-acetyloxycinnamyl amide The examples listed below are provided to the sole purpose of presenting certain specific achievements of this invention and by no means should they be held as a limitation to the scope thereof.

EXAMPLES

Example 1

Synthesis of 3-formyl-4-methoxycinnamic acid

2-Methoxy-5-iodobenzaldehyde (1.0 g, 3.82 mmol) is dissolved in 25 ml of acetonitrile and oxygen is removed by bubbling nitrogen through the solution. Triethylamine (3.71 ml, 26.7 mmol) and methyl acrylate (0.686, ml, 7.63 mmol) are added dropwise with stirring to the solution, followed by four portions of 0.0214 g of tri-o-tolylphosphine (0.095 mmol) and 0.008 g of palladium (II) acetate (0.047 mmol) at 1 hour intervals. The mixture is then heated at 65-70° C. for 4 hours, volatiles are removed by distillation and the residue is dissolved in dichloromethane. The resulting solution is percolated through silica gel eluting with a mixture of hexane-ethyl acetate (6:4). The percolate is evaporated to dryness, re-dissolved in 20 ml of methanol and 10 ml of 20% aqueous potassium carbonate solution added. The mixture is stirred for 6 hours at room temperature and concentrated under reduced pressure to a third of its volume. The solution is taken to a pH value of 1 with concentrated hydrochloride acid and the precipitate is filtered and recrystallized from isopropanol, to give 0.472 g of 3-formyl-4-methoxycinnamic acid (2.29 mmol) as a crystalline white solid. A second harvest obtained by concentration of the mother liquor gave an additional 0.105 g.

M.p. 223-225° C.; $^1$H NMR spectrum (DMSO-$d_6$, 500 MHz): 12.35 (1H, s, COOH), 10.33 (1H, s, ArC(O)H), 8.03 (1H, dd, J 8.8, 2.4, H-6), 7.93 (1H, d, J 2.4, H-2), 7.59 (1H, d, J 16.0, H—C═C—C═O), 7.28 (1H, d, J 8.8, H-5), 6.47 (1H, d, J 16.0, H—C═C═O), 3.96 (3H, s, CH$_3$O); $^{13}$C NMR spectrum (DMSO-$d_6$, 125 MHz): 188.9 (ArCHO), 167.6 (COOH), 162.6 (C-4), 142.6 (Ar—C═), 135.6 (C-6), 128.2 (C-2), 126.9 (C-1), 124.2 (C-3), 118.3 (═C—CO), 113.4 (C-5), 56.4 (CH$_3$O); mass spectrum (70 eV): m/z (%) 206 (18, M$^+$), 81 (33), 69 (100), 57 (25), 55 (33), 43 (39), 41 (58).

Example 2

Synthesis of N-isopropyl-3-(difluoromethyl)-4-methoxycinnamyl amide

A solution of Deoxofluor 50% in toluene (0.107 ml, 0.435 mmol) is added dropwise to a suspension of 0.030 g of 3-formyl-4-methoxycinnamic acid (0.145 mmol) in 0.4 ml of dry dichloromethane under an argon atmosphere, obtained as shown in example 1. The reaction mixture is stirred for 45 minutes at room temperature, diluted with 2 ml of dry dichloromethane and subsequently percolated through 2.5 g of silica gel under an argon atmosphere. The silica gel bed is rinsed with 8 ml of dry dichloromethane and the resulting solution is concentrated under a nitrogen flow to a final volume of 1 ml. Isopropylamine (0.0373 g, 0.435 mmol) and triethylamine (0.061 ml, 0.435 mmol) are added and the mixture is subsequently stirred for 1 hour at room temperature. The solution is diluted with 10 ml of dichloromethane, washed twice with hydrochloric acid and once with water and the solvent is evaporated under reduced pressure. The resulting solid is purified by column chromatography on silica gel, eluting with mixtures ethyl acetate-hexane of increasing polarity to give 0.025 g of N-isopropyl-3-(difluoromethyl)-4-methoxycinnamyl amide as a crystalline white solid.

M.p. 113-114° C.; $^1$H NMR spectrum (Cl$_3$CD, 500 MHz): 7.73 (1H, broad signal, H-2), 7.57 (1H, d, J 15.6, H—C═C—C═O), 7.51 (1H, m, H-6), 6.92 (1H, t, J 55.5, H—CF$_2$), 6.91 (1H, m, H-5), 6.31 (1H, d, J 15.5, H—C—C═O), 5.57 (1H, d, J 6.8, NH), 4.22 (1H, d hept, J 7.8, 6.5, H—C—N), 3.89 (3H, s, CH$_3$O), 1.22 (6H, d, J 6.6, (CH$_3$)$_2$C); $^{13}$C NMR spectrum (Cl$_3$CD, 125 MHz): 165.1 (s, C═O), 158.3 (t, J 5.8, C-4), 139.6 (s, Ar—C═), 132.4 (s, C-6), 127.9 (s, C-1), 125.0 (t, J 5.9, C-2), 123.3 (t, J 22.2, C3), 120.1 (s, ═C—CO), 111.3 (t, J 236, CF$_2$), 111.3 (s, C-5), 56.0 (s, CH$_3$O), 41.7 (s, C—N), 23.0 (s, (CH$_3$)$_2$C); mass spectrum (70 eV): m/z (%) 269 (57, M$^+$), 211 (100), 183 (23), 132 (19), 58 (34).

Example 3

Synthesis of N-methoxy-N-methyl-3-(difluoromethyl)-4-methoxycinnamyl amide

The procedure described under example 2 is followed using 0.030 g of 3-formyl-4-methoxycinnamic acid (0.145 mmol), 0.107 ml of a Deoxofluor solution 50% in toluene (0.435 mmol), 0.043 g of N,O-dimethylhydroxylamine hydrochloride (0.435 mmol) and 0.082 ml of triethylamine (0.580 mmol). N-methoxy-N-methyl-3-(difluoromethyl)-4-methoxycinnamyl amide (0.026 g) is obtained as a crystalline white solid.

M.p. 101° C.; $^1$H NMR spectrum (Cl$_3$CD, 500 MHz): 7.83-7.80 (1H, m, H-2), 7.69 (1H, d, J 15.8, H—C═C—C═O), 7.62-7.58 (1H, m, H-6), 6.96 (2H, d, J 15.8, H—C—C═O), 6.96-6.93 (1H, m, H-5), 6.94 (1H, t, J 55.5, HCF$_2$), 3.91 (3H, s, 4-CH$_3$O), 3.78 (3H, s, CH$_3$O—N), 3.31 (3H, s, N—CH$_3$); $^{13}$C NMR spectrum (Cl$_3$CD, 125 MHz): 167.1 (s, C═O), 158.5 (t, J 5.7, C-4), 142.4 (s, Ar—C═), 132.7 (s, C-6), 128.1 (s, C-1), 125.5 (t, J 5.9, C-2), 123.3 (t, J 22.1, C-3), 114.8 (s, ═C—CO), 111.4 (t, J 236, CF$_2$), 111.3 (s, C-5), 62.1 (s, CH$_3$O—N), 56.0 (s, 4-CH$_3$O), 32.7 (s, N—CH$_3$); mass spectrum (70 eV): m/z (%) 271 (3.4, M$^+$), 211 (100), 183 (18), 132 (12).

Example 4

Synthesis of N-isobutyl-3-(difluoromethyl)-4-methoxycinnamyl amide

The procedure described under example 2 is followed using 0.030 g of 3-formyl-4-methoxy-cinnamic acid (0.145 mmol), 0.107 ml of a Deoxofluor solution 50% in toluene (0.435 mmol), 0.044 g of isobutylamine (0.435 mmol) and 0.061 ml of triethylamine (0.435 mmol). N-isobutyl-3-(difluoromethyl)-4-methoxycinnamyl amide (0.025 g) is obtained as a crystalline white solid.

M.p. 145-146° C.; $^1$H NMR spectrum (Cl$_3$CD, 500 MHz): 7.77-7.72 (1H, m, H-2), 7.59 (1H, d, J 15.5, H—C═C—C═O), 7.56-7.49 (1H, m, H-6), 6.93 (1H, t, J 55.5, HCF$_2$), 6.94-6.90 (1H, m, H-5), 6.35 (1H, d, J 15.5, H—C—C═O), 5.74 (1H, t, J 5.4, NH), 3.89 (3H, s, CH$_3$O), 3.23 (2H, dd, J 6.7, 6.2, CH$_2$N), 1.92-1.77 (1H, m, CH(CH$_3$)$_2$), 0.96 (6H, d, J 6.7, CH(CH$_3$)$_2$); $^{13}$C NMR spectrum (Cl$_3$CD, 125 MHz): 166.0 (s, C═O), 158.3 (t, J 5.7, C-4), 139.8 (s, Ar—C═), 132.5 (s, C-6), 127.8 (s, C-1), 125.0 (t, J 5.9, C-2), 123.3 (t, J 22.3, C-3), 119.9 (s, ═C—CO), 111.3 (t, J 236, CF$_2$), 111.3 (s, C-5), 56.0 (s, CH$_3$O), 47.2 (s, CH$_2$N), 28.8 (s, CH(CH$_3$)$_2$), 20.3 (s, CH(CH$_3$)$_2$); mass spectrum (70 eV): m/z (%) 283 (30, M$^+$), 226 (53), 211 (100), 183 (22), 132 (20), 43 (18).

Example 5

Synthesis of N-isopentyl-3-(difluoromethyl)-4-methoxycinnamyl amide

The procedure described under example 2 is followed using 0.030 g of 3-formyl-4-methoxycinnamic acid (0.145 mmol), 0.107 ml of a Deoxofluor solution 50% in toluene (0.435 mmol), 0.051 g of isopentylamine (0.435 mmol) and 0.061 ml of triethylamine (0.435 mmol). N-isopentyl-3-(difluoromethyl)-4-methoxycinnamyl amide (0.027 g) is obtained as a crystalline white solid.

M.p. 110-111° C.; $^1$H NMR spectrum (500 MHz, CDCl$_3$) 7.80-7.68 (1H, m, H2), 7.58 (1H, d, J 15.5, H—C=C—C=O), 7.55-7.49 (1H, m, H6), 6.92 (1H, t, J 55.5, HCF$_2$), 6.97-6.85 (1H, m, H5), 6.33 (1H, d, J 15.5, H—C=C=O), 5.71 (1H, t, J 5.6, NH), 3.89 (3H, s, CH$_3$O), 3.41 (2H, dt, J 7.4, 6.0, CH$_2$N), 1.72-1.61 (1H, m, CH(CH$_3$)$_2$), 1.46 (2H, dt, J 8.5, 7.0, CH$_2$CH(CH$_3$)$_2$), 0.94 (6H, d, J 6.6, CH(CH$_3$)$_2$); $^{13}$C NMR spectrum (126 MHz, CDCl$_3$) 166.0 (s, C=O), 158.3 (t, J 5.7, C4), 139.7 (s, Ar—C=), 132.4 (t, J 1.9, C6), 127.8 (s, C1), 125.0 (t, J 5.9, C2), 123.2 (t, J 22.2, C3), 119.9 (s, =C—CO), 111.3 (t, J 236.2, CF$_2$), 111.3 (s, C5), 56.0 (s, CH$_3$O), 38.7 (s, CH$_2$CH(CH$_3$)$_2$), 38.2 (s, CH$_2$N), 26.0 (s, CH(CH$_3$)$_2$), 22.60 (s, CH(CH$_3$)$_2$); mass spectrum (70 eV): m/z (%) 297 (30, M$^+$), 241 (44), 240 (32), 226 (22), 211 (100), 183 (27), 132 (25).

Example 6

Synthesis of N,N'-bis[3-(difluoromethyl)-4-methoxy-cinnamoyl]piperazine

The procedure described under example 2 is followed using 0.030 g of 3-formyl-4-methoxycinnamic acid (0.145 mmol), 0.107 ml of a Deoxofluor solution 50% in toluene (0.435 mmol), 0.015 g of piperazonium diacetate (0.073 mmol) and 0.102 ml of triethylamine (0.73 mmol). N,N'-bis[3-(difluoromethyl)-4-methoxycinnamoyl]piperazine (0.025 g) is obtained as a crystalline white solid.

M.p. 259-261° C.; $^1$H NMR spectrum (500 MHz, CDCl$_3$+10% CD$_3$OD) 7.80 (2H, m, H2), 7.66 (2H, d, J 15.3, H—C=C—C=O), 7.65-7.61 (2H, m, H6), 7.03-6.99 (2H, m, H5), 6.96 (2H, t, J 55.5, HCF$_2$), 6.88 (2H, d, J 15.4, H—C—C=O), 3.93 (6H, s, CH$_3$O), 3.86-3.76 (8H, m, CH$_2$NCH$_2$); $^{13}$C NMR spectrum (126 MHz, CDCl$_3$) 166.3 (s, C=O), 158.5 (t, J 5.6, C4), 142.8 (s, Ar—C=), 132.4 (broad singlet, C6), 127.44 (s, C1), 125.2 (, C2), 123.1 (t, J 22.2, C3), 114.8 (s, =C—CO), 111.3 (s, C5), 111.1 (t, broad singlet J 236.1, CF$_2$), 55.7 (s, CH$_3$O), 45.4 (broad singlet, CH$_2$NCH$_2$), 42.2 (broad singlet, CH$_2$NCH$_2$); mass spectrum (ESI+): m/z 507.1892 ([M+H]$^+$, calculated for C$_{26}$H$_{27}$F$_4$N$_2$O$_4^+$ 507.1902); 211.0558 (100); 183.0610 (31), 160.0515 (4).

Example 7

Synthesis of N,N'-bis[3-(difluoromethyl)-4-methoxy-cinnamoyl]-1,3-propanamine

The procedure described under example 2 is followed using 0.030 g of 3-formyl-4-methoxycinnamic acid (0.145 mmol), 0.107 ml of a Deoxofluor solution 50% in toluene (0.435 mmol), 0.055 g of 1,3-diaminopropane (0.065 mmol) and 0.061 ml of triethylamine (0.73 mmol). N,N'-bis[3-(difluoromethyl)-4-methoxycinnamoyl]-1,3-propanamine (0.019 g) is obtained as a crystalline white solid.

M.p. 174-175° C.; $^1$H NMR spectrum (500 MHz, CDCl$_3$+10% CD$_3$OD) 7.74 (2H, m, H-2), 7.56 (2H, d, J 15.8, H—C=C—C=O), 7.57-7.53 (2H, m, H-6), 6.94-6.90 (2H, m, H-5), 6.92 (2H, t, J 55.5, HCF$_2$), 6.43 (2H, d, J 15.7, H—C—C=O), 3.90 (6H, s, CH$_3$O), 3.45-3.35 (4H, m, N—CH$_2$—CH$_2$—CH$_2$—N), 1.80-1.74 (2H, m, N—CH$_2$—CH$_2$—CH$_2$—N); $^{13}$C NMR spectrum (126 MHz, CDCl$_3$+10% CD$_3$OD) 167.2 (s, C=O), 158.3 (t, J 5.6, C-4), 139.8 (s, Ar—C=), 132.1 (s, C-6), 127.6 (s, C-1), 125.4 (t, J 5.8, C-2), 123.1 (t, J 22.1, C-3), 119.6 (s, =C—CO), 111.3 (t, J 236.2, CF$_2$), 111.3 (s, C-5), 55.9 (s, CH$_3$O), 36.48 (s, N—C—C—C—N), 29.34 (s, N—C=C—C—N); mass spectrum (ESI+): m/z 495.1893 ([M+H]$^+$, calculated for C$_{25}$H$_{27}$F$_4$N$_2$O$_4^+$ 495.1902); 268.1155 (4); 211.0570 (100); 183.0614 (13).

Example 8

Synthesis of N-methyl-3-(difluoromethyl)-4-methoxycinnamyl amide

The procedure described under example 2 is followed using 0.030 g of 3-formyl-4-methoxycinnamic acid (0.145 mmol), 0.107 ml of a Deoxofluor solution 50% in toluene (0.435 mmol), 0.030 g of methylamine hydrochloride (0.436 mmol) and 0.082 ml of triethylamine (0.58 mmol). N-methyl-3-(difluoromethyl)-4-methoxycinnamyl amide (0.021 g) is obtained as a crystalline white solid.

M.p. 169-171° C.; $^1$H NMR spectrum (500 MHz, CDCl$_3$+10% CD$_3$OD) 7.76-7.71 (1H, m, H-2), 7.57-7.54 (1H, m, H-6), 7.53 (1H, d, J 15.5, H—C=C—C=O), 6.97-6.93 (1H, m, H-5), 6.93 (1H, t, J 55.5, HCF$_2$), 6.40 (1H, d, J 15.7, H—C—C=O), 3.90 (3H, s, CH$_3$O), 2.89 (3H, s, CH$_3$N); $^{13}$C NMR spectrum (126 MHz, CDCl$_3$+10% CD$_3$OD) 167.52 (s, C=O), 158.21 (t, J 5.7, C-4), 139.38 (s, Ar—C=), 132.16 (s, C-6), 127.59 (s, C-1), 124.97 (t, J 5.9, C-2), 123.03 (t, J 22.2, C-3), 119.31 (s, =C—CO), 111.23 (t, J 236.1, CF$_2$), 111.22 (s, C-5), 55.77 (s, CH$_3$O), 26.18 (s, CH$_3$N); mass spectrum (70 eV): m/z (%) 241 (55, M$^+$), 240 (26), 211 (100), 183 (25), 132 (22).

Example 9

Synthesis of N-(2-phenymethyl)-3-(difluoromethyl)-4-methoxycinnamyl amide

The procedure described under example 2 is followed using 0.030 g of 3-formyl-4-methoxycinnamic acid (0.145 mmol), 0.107 ml of a Deoxofluor solution 50% in toluene (0.435 mmol), 0.055 g of phenyethylamine (0.435 mmol) and 0.061 ml of triethylamine (0.435 mmol). N-(2-phenymethyl)-3-(difluoromethyl)-4-methoxycinnamyl amide (0.029 g) is obtained as a crystalline white solid.

M.p. 104-105° C.; $^1$H NMR spectrum (Cl$_3$CD, 500 MHz): 7.72-7.71 (1H, m, H-2), 7.57 (1H, d, J 15.6, H—C=C—C=O), 7.52-7.49 (1H, m, H-6), 7.35-7.21 (5H, C$_6$H$_5$CH$_2$CH$_2$N), 6.91 (1H, t, J 55.5, HCF$_2$), 6.90 (1H, m, H-5), 6.26 (1H, d, J 15.5, H—C—C=O), 5.74 (1H, broad triplet, J 5.3, NH), 3.88 (3H, s, CH$_3$O), 3.71-3.62 (2H, m, PhCH$_2$CH$_2$N), 2.89 (2H, t, J 6.9, PhCH$_2$CH$_2$N); $^{13}$C NMR spectrum (Cl$_3$CD, 125 MHz): 166.0 (s, C=O), 158.3 (t, J 5.7, C-4), 139.9 (s, Ar—C=), 139.0 (s, C—CH$_2$—CH$_2$N), 132.4 (s, C-6), 128.9 (s, CH=CH—CH=C—CH$_2$—), 128.8 (s, CH=CH—CH=C—CH$_2$—), 127.7 (s, C-1), 126.7 (s, CH=CH—CH=C—CH$_2$—), 125.1 (t, J 5.9, C-2), 123.2 (t, J 22.2, C-3), 119.6 (s, =C—CO), 111.3 (t, J 236.3, CF2), 111.3 (s, C-5), 56.0 (s, CH$_3$O), 40.9 (s, CH$_2$—CH$_2$N), 35.8 (s, CH$_2$—CH$_2$N); mass spectrum (70 eV): m/z (%) 331 (34, M$^+$), 226 (32), 211 (100), 183 (19), 132 (16), 104 (17), 91 (47).

Example 10

Synthesis of N-pheny-3-(difluoromethyl)-4-methoxycinnamyl amide

The procedure described under example 2 is followed using 0.030 g of 3-formyl-4-methoxycinnamic acid (0.145 mmol), 0.107 ml of a Deoxofluor solution 50% in toluene (0.435 mmol), 0.040 g of aniline (0.435 mmol) and 0.061 ml of triethylamine (0.435 mmol). N-phenyl-3-(difluoromethyl)-4-methoxycinnamyl amide (0.022 g) is obtained as a crystalline white solid.

M.p. 135-136° C.; $^1$H NMR spectrum (500 MHz, Cl$_3$CD): 7.77-7.74 (1H, m, H-2), 7.70 (1H, d, J 15.5, H—C=C—C=O), 7.65-7.62 (2H, m, CH=C(N)—CH), 7.60 (1H, broad singlet, PhNH), 7.54-7.50 (1H, m, H-6), 7.37-7.31 (2H, m, CH—CH=C(N)—CH—CH), 7.14-7.10 (1H, m, CH=CH—CH=C(N)), 6.92 (1H, t, J 55.5, HCF$_2$), 6.92-6.88 (1H, m, H-5), 6.50 (1H, d, J 15.5, H—C—C=O), 3.89 (3H, s, CH$_3$O); $^{13}$C NMR spectrum (Cl$_3$CD, 125 MHz): 164.0 (s, C=O), 158.5 (t, J 5.6, C-4), 141.1 (s, Ar—C=), 138.1 (s, CH=C(N)—CH), 132.5 (s, C-6), 129.1 (s, CH—CH=C(N)), 127.4 (s, C-1), 125.2 (t, J 5.7, C-2), 124.4 (s, CH=CH—CH=C(N)), 123.2 (t, J 22.2, C-3), 120.0 (s, CH=CH—CH=C(N)), 119.7 (s, =C—CO), 111.2 (s, C-5), 111.2 (t, J 236.4, CF$_2$), 55.9 (s, CH$_3$O); mass spectrum (70 eV): m/z (%) 331 (34, M$^+$), 303 (25), 211 (100), 183 (17), 132 (15), 93 (19).

Example 11

Synthesis of N-cyclohexyl-3-(difluoromethyl)-4-methoxycinnamyl amide

The procedure described under example 2 is followed using 0.030 g of 3-formyl-4-methoxycinnamic acid (0.145 mmol), 0.107 ml of a Deoxofluor solution 50% in toluene (0.435 mmol), 0.050 g of cyclohexylamine (0.435 mmol) and 0.061 ml of triethylamine (0.435 mmol). N-ciclohexyl-3-(difluoromethyl)-4-methoxycinnamyl amide (0.034 g) is obtained as a crystalline white solid.

M.p. 181-183° C.; $^1$H NMR spectrum (500 MHz, Cl$_3$CD): 7.75-7.73 (1H, m, H-2), 7.58 (1H, d, J 15.5, H—C=C—C=O), 7.55-7.49 (1H, m, H-6), 6.92 (1H, t, J 55.5, HCF$_2$), 6.93-6.90 (1H, m, H-5), 6.32 (1H, d, J 15.5, H—C—C=O), 5.61 (1H, broad d, J 6.2, NH), 3.97-3.90 (1H, m, Cyclohexyl H-1ax), 3.89 (3H, s, CH$_3$O), 2.04-1.92 (2H, m, Cyclohexyl H-2ec), 1.79-1.69 (2H, m, Cyclohexyl H-3ec), 1.68-1.59 (1H, m, Cyclohexyl H-4ec), 1.48-1.34 (2H, m, Cyclohexyl H-3ax), 1.20 (2H, m, Cyclohexyl H-2ax), 1.19 (1H, m, Cyclohexyl H-4ax); $^{13}$C NMR spectrum (Cl$_3$CD, 125 MHz): 165.0 (s, C=O), 158.3 (t, J 5.6, C-4), 139.6 (s, Ar—C=), 132.4 (s, C-6), 127.9 (s, C-1), 125.0 (t, J 5.8, C-2), 123.3 (t, J 22.3, C-3), 120.2 (s, =C—CO), 111.3 (t, J 236.2, CF2), 111.3 (s, C-5), 56.0 (s, CH$_3$O), 48.5 (s, Cyclohexyl C-1), 33.4 (s, Cyclohexyl C-2), 25.7 (s, Cyclohexyl C-4), 25.0 (s, Cyclohexyl C-3); mass spectrum (70 eV): m/z (%) 309 (62, M$^+$), 226 (64), 211 (100), 183 (33), 132 (25), 98 (39).

Example 12

Synthesis of N-[3-(difluoromethyl)-4-methoxy-cinnamoyl]morpholine

The procedure described under example 2 is followed using 0.030 g of 3-formyl-4-methoxycinnamic acid (0.145 mmol), 0.107 ml of a Deoxofluor solution 50% in toluene (0.435 mmol), 0.0376 g of morpholine (0.435 mmol) and 0.061 ml of triethylamine (0.435 mmol). N-[3-(difluoromethyl)-4-methoxy-cinnamoyl]morpholine (0.024 g) is obtained as a crystalline white solid.

M.p. 119° C.; $^1$H NMR spectrum (500 MHz, Cl$_3$CD): 7.82-7.75 (1H, m, H-2), 7.67 (1H, d, J 15.4, H—C=C—C=O), 7.56-7.54 (1H, m, H-6), 6.94 (1H, t, J 55.5, HCF$_2$), 6.95-6.93 (1H, m, H-5), 6.78 (1H, d, J 15.4, H—C—C=O), 3.91 (3H, s, CH$_3$O), 3.79-3.66 (8H, m, Morpholyl H); $^{13}$C NMR spectrum (Cl$_3$CD, 125 MHz): 165.7 (s, C=O), 158.4 (t, J 5.7, C-4), 142.2 (s, Ar—C=), 132.7 (s, C-6), 128.1 (s, C-1), 124.9 (t, J 5.8, C-2), 123.3 (t, J 22.2, C-3), 115.4 (s, =C—CO), 111.3 (t, J 236.6, CF$_2$), 111.3 (s, C-5), 67.0 (s, CH$_2$OCH$_2$), 56.0 (s, CH$_3$O), 46.4 (s, CH$_2$NCH$_2$), 42.6 (s, CH$_2$OCH$_2$); mass spectrum (70 eV): m/z (%) 297 (53, M$^+$), 211 (100), 183 (22), 132 (15), 86 (12).

Example 13

Synthesis of N-[3-(difluoromethyl)-4-methoxycinnamoyl]N'-(isonicotinoyl)hydrazine The procedure described under example 2 is followed using 0.060 g of 3-formyl-4-methoxycinnamic acid (0.290 mmol), 0.214 ml of a Deoxofluor solution 50% in toluene (0.870 mmol), 0.060 g of isonicotinoylhydrazide (0.435 mmol) and 0.081 ml of triethylamine (0.580 mmol). N-[3-(difluoromethyl)-4-methoxycinnamoyl]N'-(isonicotinoyl) hidrazine (0.018 g) is obtained as a yellow solid.

M.p. 119-120° C.; $^1$H NMR spectrum (500 MHz, CDCl$_3$+ 10% CD$_3$OD) 8.72 (2H, d, J 4.9, H—C=N—C—H), 7.81-7.79 (2H, m, H—C—C=N—C=C—H), 7.76-7.73 (1H, m, H-2), 7.66 (1H, d, J 15.7, H—C=C—C=O), 7.61-7.56 (1H, m, H-6), 6.97-6.93 (1H, m, H-5), 6.93 (1H, t, J 55.4, HCF$_2$), 6.56 (1H, d, J 15.7, H—C—C=O), 3.91 (3H, s, CH$_3$O); $^{13}$C NMR spectrum (125 MHz, CDCl$_3$+10% CD$_3$OD) 164.4 (s, C=C—C=O), 163.2 (s, ArC=O), 158.7 (t, J 5.3, C-4), 150.0 (s, C=N—C), 141.8 (s, Ar—C=C), 139.5 (s, C=C—C=N), 132.2 (s, C-6), 127.1 (s, C-1), 125.6 (t, J 5.8, C-2), 123.2 (t, J 22.1, C-3), 121.6 (s, C—C=N—C=C), 115.8 (s, =C—CO), 111.3 (s, C-5), 111.1 (t, J 236.2, CF$_2$), 55.8 (s, CH$_3$O); mass spectrum (70 eV): m/z (%) 211 (51), 132 (25), 106 (53), 78 (100), 51 (58).

Example 14

Synthesis of 3-formyl-4-acetyloxycinnamic acid

2-Acetyloxy-5-iodobenzaldehyde (0.2 g, 0.69 mmol) is dissolved in 25 ml of acetonitrile and oxygen is removed by bubbling nitrogen through the solution. Triethylamine (0.673 ml, 4.82 mmol) and acrylic acid (0.095 ml, 1.38 mmol) are added dropwise with stirring, followed by 0.016 g of tri-o-tolylphosphine (0.069 mmol) and 0.008 of palladium(II) acetate (0.047 mmol). The mixture is heated at 65-70° C. for 4 hours, volatiles are removed by distillation and the residue is purified by column chromatography on silica gel, eluting with mixtures of ethyl acetate-hexane of increasing polarity. 3-Formyl-4-acetyloxycinnamic acid (0.095 g) is obtained as a white solid.

M.p. 205-207° C.; $^1$H NMR spectrum (DMSO-d$_6$, 500 MHz): 12.53 (1H, s, COOH), 10.07 (1H, s, ArC(O)H), 8.22 (1H, d, J 2.3, H-2), 8.08 (1H, dd, J 8.6, 2.2, H-6), 7.67 (1H, d, J 16.0, H—C=C—C=O), 7.36 (1H, d, J 8.4, H-5), 6.63 (1H, d, J 16.1, H—C—C=O), 2.35 (3H, s, CH$_3$C(O)OAr); $^{13}$C NMR spectrum (DMSO-d$_6$, 125 MHz): 189.9 (ArCHO), 169.1 (CH$_3$C(O)OAr), 167.3 (COOH), 151.7 (C-4), 141.8 (Ar—C=), 134.7 (C-6), 132.8 (C-1), 131.2 (C-2), 128.2 (C-3), 124.5 (C-5), 120.9 (=C—CO), 20.7 (CH$_3$C(O)OAr); mass spectrum (70 eV): m/z (%) 234 (1, M$^+$), 192 (23), 146 (9), 91 (20), 89 (45), 63 (19), 43 (100).

Example 15

Synthesis of N-isopropyl-3-(difluoromethyl)-4-acetyloxy cinnamyl amide]

The procedure described under example 2 is followed using 0.030 g of 3-formyl-4-acetyloxycinnamic acid (0.128 mmol), 0.095 ml of a Deoxofluor solution 50% in toluene (0.386 mmol), 0.033 ml of isopropylamine (0.386 mmol) and 0.054 ml of triethylamine (0.386 mmol). N-isopropyl-3-(difluoromethyl)-4-acetyloxycinnamyl amide (0.018 g) is obtained as a white solid.

M.p. 131-133° C.; $^1$H NMR spectrum (Cl$_3$CD, 500 MHz): 7.76-7.71 (1H, m, H-2), 7.60 (1H, d, J 15.5, H—C═C—C═O), 7.61-7.55 (1H, m, H-6), 7.23-7.18 (1H, m, H-5), 6.74 (1H, t, J 55.2, HCF$_2$), 6.36 (1H, d, J 15.6, H—C═C═O), 5.49 (1H, d, J 7.8, NH), 4.28-4.17 (1H, m, H—C—N), 2.34 (3H, s, CH$_3$C(O)OAr), 1.23 (6H, d, J 6.6, (CH$_3$)$_2$C); $^{13}$C NMR spectrum (Cl$_3$CD, 125 MHz): 168.8 (s, CH$_3$C(O)OAr), 164.5 (s, —C(O)NH), 149.1 (t, J 5.2, C-4), 138.9 (s, Ar—C═), 133.4 (s, C-1), 131.2 (broad singlet, C-6), 127.0 (t, J 22.6, C-3), 125.5 (t, J 6.4, C-2), 123.8 (s, C-5), 122.6 (s, ═C—CO), 111.6 (t, J 238.9, CF$_2$), 41.9 (s, C—N), 22.96 (s, (CH$_3$)$_2$C), 20.96 (s, CH$_3$C(O)OAr); mass spectrum (70 eV): m/z (%) 298 (23, M+1), 297 (18, M$^+$), 255 (88), 197 (68), 177 (44), 101 (30), 58 (100), 43 (60).

Example 16

Determination of the Minimum Inhibitory Concentration

The Minimum Inhibitory Concentration (MIC), which is defined as the lowest antimicrobial agent concentration inhibiting the visible growth of a microorganism following its incubation, was subsequently determined.

For the purpose of such determination, the compounds under study were tested on the strains listed in Table 3 with the antibiotics (AB) stated as reference in the table.

The test was conducted on a plate on the basis of a 1×10$^5$ CFU/ml inoculum concentration, with negative, positive and sterility controls being simultaneously performed. Different concentrations of the compounds under study were tested, as shown on the last column included in Table 3 (working solution).

Following incubation at 32.5±2.5° C. for a 24 h period (48 h in the case of *C. sporogenes* and 72 h in the case of *M. smegmatis*), the plates were visually read. The appearance of turbidity and/or the formation of a growth point at the microtube bottom were held as a positive result.

TABLE 3

Strains employed in antibacterial agent tests

| Genera/Species | ATCC | Reference (lower resistance according to WHONET) | MIC (for WHO antibiotics) | Working solution (µg/ml) |
|---|---|---|---|---|
| Gram + Coccobacilli | | | | |
| Staphylococcus Aureus | 29737 | Vancomycin | 0.5-2.0 | 64, 32, 8, 2, 1, 0.5, 0.25, 0.125 |
| Streptococcus pneumoniae | 10015 | Ampicillin (sodium) | ≤0.5 | 64, 32, 8, 2, 1, 0.5 |

TABLE 3-continued

Strains employed in antibacterial agent tests

| Genera/Species | ATCC | Reference (lower resistance according to WHONET) | MIC (for WHO antibiotics) | Working solution (µg/ml) |
|---|---|---|---|---|
| Streptococcus pyogenes | 8133 | Penicillin G (potassium salt)/ Ampicillin PF | ≤0.125 | 128, 64, 32, 8, 2, 1, 0.5 |
| Enterococcus faecalis | 29212 | Vancomycin | 1.0-4.0 | 64, 32, 16, 8, 4, 1, 0.5 |
| Gram – Bacilli | | | | |
| Shigella boydii | 12027 | Phosphomycin | ≤4.0 | 64, 32, 8, 2, 1, 0.5 |
| Escherichia Coli | 8739 | Imipenem | ≤2.0 | 64, 32, 16, 4, 2, 1, 0.5 |
| Shigella flexneri | 11836 | Phosphomycin | ≤4.0 | 64, 32, 8, 2, 1, 0.5 |
| Pseudomona aeruginosa | 9027 | Imipenem | 1.0-4.0 | 64, 32, 16, 8, 4, 1, 0.5 |
| Klebsiella pneumoniae | 10273 | Imipenem | ≤2.0 | 64, 32, 16, 8, 4, 2, 1 |
| Proteus mirabilis | 10005 | Imipenem | ≤2.0 | 128, 64, 32, 16, 8, 4, 2, 1 |
| Enterobacter cloacae | 35587 | Imipenem | ≤2.0 | 64, 32, 16, 8, 4, 2, 1 |
| Acinetobacter guillouiae | 11171 | Minocyclin | 0.06-8.0 | 128, 64, 32, 16, 8, 2, 1, 0.5 |
| Gram + Bacilli | | | | |
| Mycobacterium smegmatis | 607 | Imipenem | ≤4.0 | 64, 32, 16, 8, 4, 2, 1, 0.5 |
| Clostridium sporogenes | 19404 | Vancomycin | ≤2.0/≤0.2 | 64, 32, 16, 8, 4, 2, 1 |

The invention claimed is:
1. A compound of the following structural formula:

a pharmaceutically acceptable salt or prodrug, wherein
R$_1$ is selected from the group consisting of H, a linear or branched (C1-C5) alkyl group and a COR$_4$ group;
R$_2$ is selected from the group consisting of H, a linear or branched (C1-C5) alkyl group and a COR$_5$ group;
R$_3$ is selected from the group consisting of H, a linear or branched (C1-C5)alkyl group, a linear or branched (C1-C5)-O-alkyl group, a cycloalkyl of (C5-C6) carbon atoms, an aryl group, and an aryl (C1-C5) alkyl group wherein the aryl group can be an unsubstituted aryl or an aryl substituted with one or more R$_6$ groups and an NHCOR$_5$ group, or the R$_2$ and R$_3$ groups together with N may form a substituted or unsubstituted piperidine, morpholine or piperazine group;
R$_4$ is selected from the group consisting of H and a (C1-C5)alkyl group;
R$_5$ is an unsubstituted aryl group or an aryl group substituted with one or more R$_6$, linear or branched(C1-C5) alkyl or a pyridine group; and

R6 is selected from the group consisting of (C1-C5)alkyl groups, halogen and nitro, provided that $R_1$, $R_2$ and $R_3$ are not H atoms at the same time.

2. A compound according to claim 1, a pharmaceutically acceptable salt or prodrug thereof, wherein it is selected from the following compounds:

3. A pharmaceutical composition comprising at least one compound or pharmaceutically acceptable salt or prodrug thereof, according to claim 2, and pharmaceutically acceptable excipients.

4. A pharmaceutical composition comprising at least one compound according to claim 1 and pharmaceutically acceptable excipients.

5. A pharmaceutical composition comprising at least one compound or pharmaceutically acceptable salt or prodrug thereof, according to claim 1, further comprising at least another therapeutically active substance different from the first compound.

6. A method for treating infections, comprising the administration to a human or animal of a compound or a pharmaceutically acceptable salt or prodrug thereof, according to claim 1.

7. A method for treating infections, comprising the administration to a human or animal of a pharmaceutical composition according to claim 2.

8. A process for the preparation of compounds of claim 1, comprising the following steps:
   a) Heck coupling 2-methoxy-5-iodobenzaldehyde or 2 acetyloxy-5-iodobenzaldehyde with acrylic acid or coupling 2 methoxy-5-iodobenzaldehyde with an ester of acrylic acid, followed by hydrolysis of the ester product;
   b) treating the cinnamic acid derivative resulting from step a) with a fluorinating reagent; and
   c) reacting the acyl fluoride obtained from step b) with an amine of formula $HNR_2R_3$, in the presence of a base.

9. The process according to claim 8, characterized in that the ester of acrylic acid is methyl acrylate.

10. The process according to claim 8, wherein the fluorinating reagent is bis [(2-methoxyethyl)amino]sulfur trifluoride.

11. The process according to claim 8, further comprising at least one step of percolation of the mixture resulting from the fluorination reaction through a silica gel bed to obtain an acyl fluoride solution free of any fluorination reaction byproducts.

12. The process according to the claim 11, characterized in that the acyl fluoride solution free of fluorination reaction byproducts is directly treated with the amine of step (c) in the presence of a base, so as to obtain the corresponding amide.

13. The process according to claim 11, characterized in that the acyl fluoride solution free of fluorination reaction byproducts is directly treated with a salt of the amine of step (c) and a base, so as to obtain the corresponding amide.

14. The process according to claim 12, characterized in that the base is a tertiary amine selected from triethylamine, 1,4-diazabicyclo-(2,2,2)-octane and diazabicycloundecane (DBU).

\* \* \* \* \*